United States Patent [19]

Janovsky et al.

[11] 4,352,352

[45] Oct. 5, 1982

[54] HEAD GEAR MANIPULATOR FOR INVALIDS

[76] Inventors: Franz Janovsky, Flachsweg 6, Vienna A-1220; Erhard Demmer, Weinberggasse 41, Vienna A-1190, both of Austria

[21] Appl. No.: 256,791

[22] Filed: Apr. 23, 1981

[30] Foreign Application Priority Data

May 13, 1980 [AT] Austria .................................. 2564/80

[51] Int. Cl.³ .................................................. A61F 5/08
[52] U.S. Cl. ......................................... 128/76 R; 3/1.1
[58] Field of Search ............... 128/76 R, 80 R, 80 G, 128/25 R; 3/1.1, 1

[56] References Cited

U.S. PATENT DOCUMENTS 3,769,636  11/1973  Friedman .................................. 3/1.1

Primary Examiner—John D. Yasko
Attorney, Agent, or Firm—Kurt Kelman

[57] ABSTRACT

A head gear manipulator for an invalid comprises a helmet, an arm carrying a gripper, an electro-motor operating the gripper in response to muscle movements of the invalid wearing the helmet, wherein the helmet consists of a blank of thermoplastically deformable sheet material having a center portion and a plurality of arms radiating from the center portion, and a longitudinally adjustable circular band mounted over the free ends of the arms and connecting the same. A mounting is affixed to the center portion for holding the arm carrying the gripper.

9 Claims, 3 Drawing Figures

HEAD GEAR MANIPULATOR FOR INVALIDS

The present invention relates to a head gear manipulator for substantially fully incapacitated invalids and comprising a helmet worn by the invalid, an arm carrying grippings means mounted on the helmet and electromotor drive means operating the gripping means in response to certain muscle movements of the invalid.

Conventional prostheses or ortheses are useless for invalids who have lost the function of both arms and cannot restore the gripping or grasping power of their hands. If the mobility of the lower extremities remains intact, younger patients in particular make use of their feet and toes for grasping objects. This, however, has the disadvantage that such activities as writing, drawing or painting cannot be carried out in the normal sitting position of the patient. Furthermore, less agile and older invalids usually cannot be trained for such use of their feet and toes. At any rate, it always subjects the spine to heavy pressure and often interferes with proper breathing. Where the patient has also lost movement in his lower extremeties, this procedure is not available at all. Such patients sometimes can learn to carry out some limited activities by use of their mouth and teeth for gripping objects. This often leads to damage of the teeth and jaws. Furthermore, the range of vision is unduly foreshortened.

Various auxiliary instruments have been developed for wheelchair-bound invalids, such as quadruplegics, to carry out some limited activities, such as turning a radio or television apparatus on and off, opening and closing a door and the like, by operating a mechanical switch actuated by the tongue of the patient, by blowing or by sucking. Obviously, this can be used only for a strictly limited range of programmed activities and not for individual, personal activities such as writing, drawing, playing games or eating and the like.

For the latter purpose, invalids have been equipped with head gear manipulators which comprise a helmet worn by the invalid and carrying an arm whose outer end is equipped with an artificial gripper within the field of vision of the patient and at the normal distance from his or her eyes to enable the patient to see the gripper without difficulty. The gripper simulates the fingers of the patient and, using the range of movement of the head and upper body, a relatively wide range of manipulation may be effected upon operation of the gripper fingers. For instance, the gripper may grasp a figure and move it on a game board from one spot to another. It may also be used to hold a writing, drawing or painting implement and to write, draw or paint therewith by moving the held implement over a writing, drawing or painting surface or canvass by movement of the head or upper body. An eating implement may also be held by the gripper fingers so that the invalid may feed himself or herself.

The usefulness of such head gear manipulators depends on the control of the gripper movements. Since the total incapacity of the types of invalids using such manipulators prevents direct control by the patient, the gripping means are operated by electro-motor drive means in the known head gear manipulators. A suitable transmission transmits the drive of the electro-motor to the gripping mechanism and conventional switches are used to energize or de-energize the motor, or to reverse it to open and close the gripper fingers. For instance, a pull switch may be operated by a chin band attached to the helmet and pulled by moving the lower jaw. This produces unwanted motor operations when the patient moves the lower jaw during chewing or talking, for example. In addition, the chain band interferes with the placing of the helmet on the head and makes its use uncomfortable.

The helmet itself has to meet specific requirements, including light weight and good fit so that it does not slide on the head of the patient during manipulations. On the other hand, since it often is worn for hours, it should not press on the head to avoid discomfort. For these reasons, such helmets for head gear manipulators have heretofore been custom-made by highly specialized artisans having skills far beyond those of the average orthopedic mechanic or bandage maker. This has made head gear manipulators for severely handicapped invalids expensive and difficult to provide.

It is the primary object of this invention to provide a head gear manipulator of the indicated type but which enables the helmet to be mass-produced and to be adapted readily and simply to each individual wearer.

It is another important object of the invention to provide such a manipulator which can be controlled dependably and is secure against unwanted operation in the course of such activities as chewing or talking.

The above and other objects are accomplished according to the present invention with a helmet consisting of a blank of thermoplastically deformable sheet material having a center portion and a plurality of arms radiating from the center portion, the arms having free ends, and a longitudinally adjustable circular band mounted over the free arm ends and connecting the same. The band is preferably elastic and a mounting is affixed to the center portion of the helmet for holding the arm carrying the gripping means.

Such helmet blanks may be readily punched out of a length of sheet material and each punched-out blank may be suitably deformed into helmet shape under heat by bending down the radiating arms from the center portion and then interconnecting the free arm ends with the head band which is adjusted to the desired circumference.

The above and other objects, advantages and features of this invention will become more apparent from the following detailed description of a now preferred embodiment thereof, taken in conjunction with the accompanying shematic drawing wherein.

Figure 1:
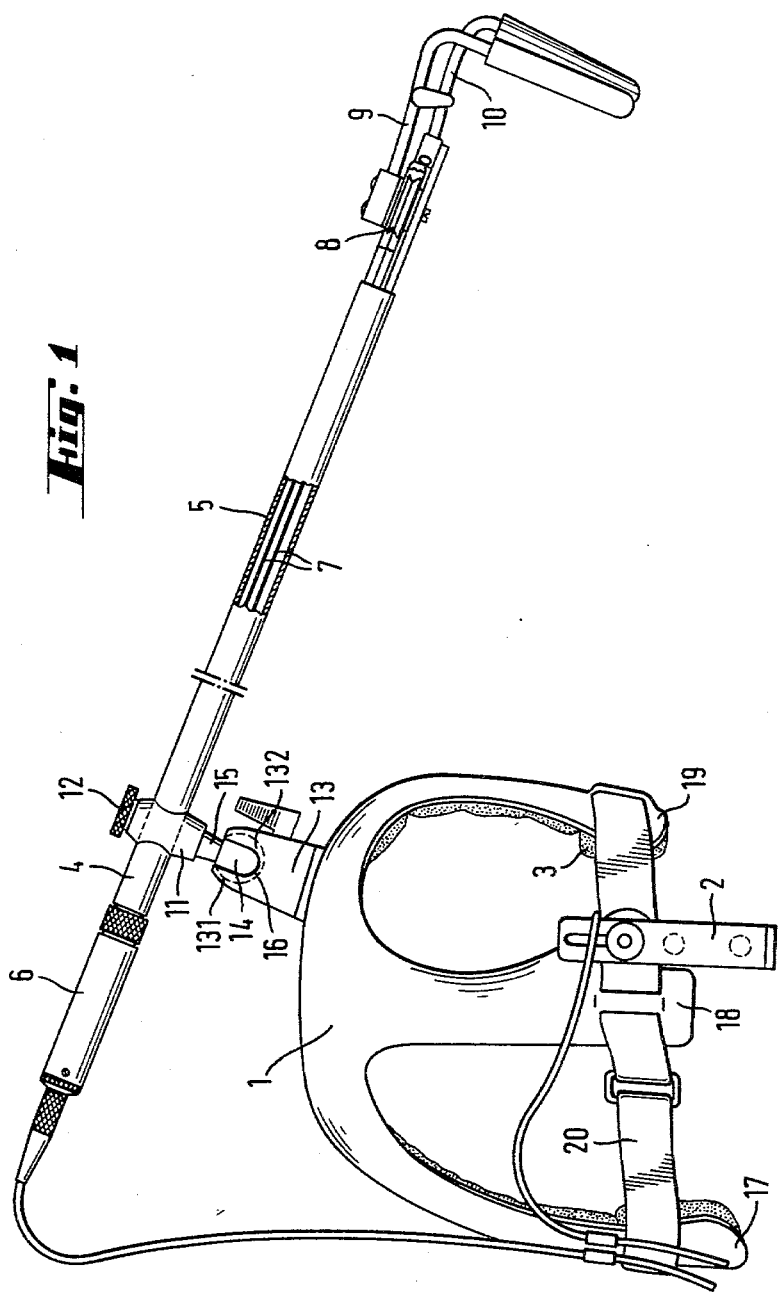
FIG. 1 illustrates a side view, partially in section, of a head gear manipulator according to the invention.

Referring now to the drawing and first to FIG. 1, the illustrated head gear manipulator comprises helmet 1 equipped with control electrode 2 and ground electrode 3. Control electrode 2 is adjustably mounted on a portion of the helmet clamped to the temples of the wearer and resiliently contacts the temples with an elastically biased carrier part. Ground electrode 3 is formed by a portion of the helmet cushioning and consists of an electrically conductive textile web or fabric arranged to contact the forehead of the invalid wearer. Manipulator arm 4 is mounted on helmet 1 and is illustrated herein as a light metal tube 5 carrying drive unit 6 at a rear end thereof. The drive unit comprises electro-motor means including a motor, a reduction bearing and a double spindle converting the rotary motion of the motor shaft into a rectilinear, reciprocatory motion. This motion is transmitted by cable lines 7 in the interior of tube 5 to pulley 8 at the front end of the tube, which re-converts the rectilinear to a rotary motion. A transmission of this general type has been described, for example, in U.S. Pat. No. 4,232,405, dated Nov. 11, 1980. The illustrated gripping means carried by arm 4 comprises movable gripping finger 9 affixed to pulley 8 and moved therewith, the movable gripping finger being arranged to cooperate for a gripping manipulation with a stationary gripping finger 10 mounted at the front end of manipulator arm 4.

Mounting 13 for holding arm 4 carrying gripping means 9, 10 is affixed to helmet 1 and, in the illustrated embodiment, the mounting has spherical socket 131 wherein ball 132 is frictionally held against free movement. The manipulator arm mounting is affixed to helmet 1 at the top of the head, preferably a little closer to the forehead than the back of the head. Stem 15 connects ball 132 of the ball-and-socket joint 131, 132 to holder 11 defining a guide bore in which manipulator arm 4 is glidably and adjustably inserted. The arm is set in the holder in the adjusted position by set screw 12 threadedly engaging holder 11 and bearing against arm 4 inserted in the bore thereof. This adjustable positioning of the manipulator arm enables its effective length to be changed at will so that the distance between gripping means 9, 10 and the eyes of the invalid wearer of helmet 1 may be adjusted to an optimum for best visibility.

The friction between ball 132 and socket 131 is sufficient to prevent the manipulator arm from moving in relation to the helmet when a relatively light gripped object is lifted by arm 4 but is not so great that it would prevent such arm movement when the invalid patient engages gripping fingers 9, 10 with a stationary surface, such as a table top, and moves the head relative thereto. Under these conditions, universal joint 131, 132 will permit manipulator arm 4 to move in response to the movement of the head. Such a joint will considerably enlarge the range of manipulations beyond that attainable with a rigid connection between the manipulator arm and the helmet.

In the preferred embodiment illustrated herein, spherical socket 131 defines two diametrically opposed slots 14 having a width corresponding to the diameter of stem 15. This enables manipulator arm 4 to be rotated abouts its axis. When gripping fingers 9, 10 are engaged with, and supported by, a stationary surface, such as a table top, a suitable rotary motion of the patient's head will produce a corresponding pivoting motion of stem 15 through one or the other slot 14. When the head motion is subsequently reversed, stem 15 is retained in engaged slot 14 and manipulator arm 4 may be rotated about its axis by a maximum arc of 90°. This enables the gripping fingers to be brought from a vertical into a horizontal position, which further enhances the gripping possibilities.

Figure 2:
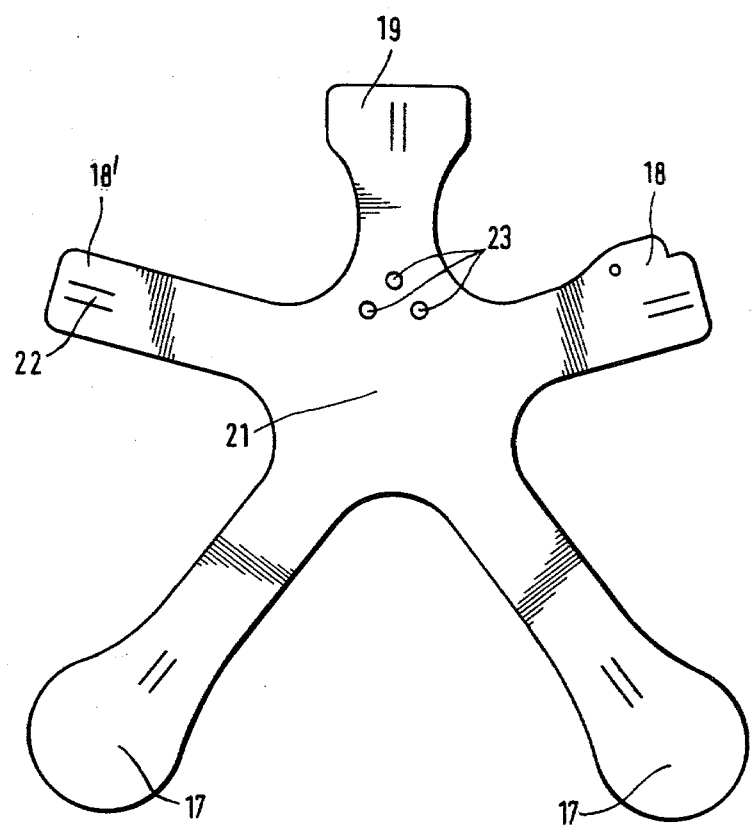
FIG. 2 is a top view of a helmet blank.

As has been pointed out hereinabove, helmet 1 consists of a blank of thermoplastically deformable sheet material whose configuration is illustrated in FIG. 2. As shown, the blank has center portion 21 and a plurality of arms 17, 18, 18' and 19 radiating from the center portion, the arms having free ends. Loops 22 formed by parallel cuts at the free arm ends receive longitudinally adjustable circular band 20 (see FIG. 1) mounted over the free arm ends and connecting the same after the arms have been suitably deformed under heat to form helmet 1 from the blank. Head band 20 is preferably elastic so that the helmet may be held firmly on the head of the wearer, the length of the band being first suitably adjusted to the head size.

The preferred helmet blank illustrated herein has five arms radiating from center portion 21, two adjacent arms 17 having enlarged free ends designed to enclose the condyles of the rear head bone of the invalid wearer of helmet 1, as indicated in FIG. 1. Two opposing arms 18, 18' have free ends arranged to contact the temples so that the helmet is clamped to the head at the temples. As shown, arm 18 has an enlargement whereon control electrode 2 is adjustably mounted, the electrode having a slot engaged by a set screw mounting the electrode on the enlargement so that the electrode may be held in selected positions on the helmet (see FIG. 1). The control electrode is resilient so that it may resiliently contact the temple. Finally, arm 19 between opposing arms 18, 18' is arranged to contact the forehead of the invalid wearer of helmet 1 and thus clamps the helmet to the forehead, the free end of arm 19 being enlarged to reduce the pressure of the forehead. Cushioned ground electrode 3 is mounted on this enlarged free end of arm 19. This ground electrode is shown as an electrically conductive part of the cushion which lines the entire helmet for added comfort.

The ready deformability of the sheet material makes it possible to use a standard blank for various head shapes and sizes, suitably shaping the blank to conform thereto while the blank is heated to enable the thermoplastically deformable material to be deformed. Perfect custom fitting may be performed on the helmet by further shaping on the head of the patient. The helmet is lined with a cushioning material and is firmly held in position on the head by longitudinally adjustable and preferably elastic head band 20 which is adjusted to the head size of the invalid wearer. The elasticity of the sheet material and of the head band makes a perfect fit of mass-produced helmets possible with a minimum of readily made adjustments. This does away with the time and expense involved in preparing custom-made helmets for head gear manipulators.

Figure 3:
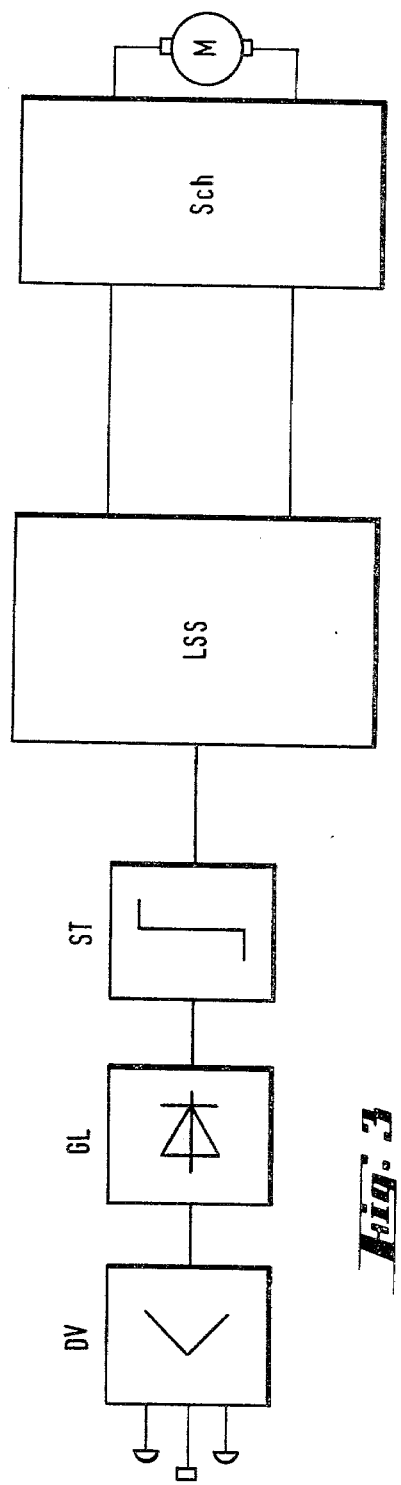
FIG. 3 is a circuit diagram of a myoelectric control for the manipulator of FIG. 1.

FIG. 3 shows a circuit diagram of one embodiment of a myo-electric control for the electro-motor drive means used in the above-described manipulator. The input circuit is constituted by differential amplifier DV connected to control electrode 2 and ground electrode 3 to receive an input signal therefrom and amplify the same. The amplified signal is transmitted from amplifier DV to rectifier GL connected thereto and the rectified signal is transmitted from the output of the rectifier to the input of Schmitt-trigger ST. The output signal of the Schmitt-trigger is transmitted to logic control circuit LSS which selects a respective control signal for transmission to switch step Sch for operation of motor M connected thereto and being mounted in drive unit 6 to turn the motor in the desired rotary direction.

The drive control is based on the following criteria:

A short muscle tensioning starts the opening movement.

A longer muscle tensioning starts the closing movement.

A renewed muscle tensioning of any duration between the two movements (stop control) deenergizes the motor and thus terminates the movement of finger 9 in the desired position.

This control makes is possible to bring the gripping means from any starting position into any desired position. It is possible for the invalid patient without any difficulty to grasp an object again if the first attempt was not entirely successful in firmly gripping the object.

The entire control together with a power source, preferably a rechargeable battery, may be built into a small box and may be carried by the invalid patient. Two cables lead from the box to the head gear manipulator. One cable connects the output of the control circuit to electro-motor M mounted on manipulator arm 4 while the second cable transmits the myoelectrical control signals from control electrode 2 to the control circuit. Control electrode is mounted on one side of helmet 1, which makes a separate mounting unnecessary. Preferably, control electrode 2 is so arranged that it resiliently contacts the head of the invalid patient near or at a temple so that the myoelectrical control signals are desired from m. temporalis. In this manner, the grippring means control is substantially free of any influence from other head or face muscle movements. Therefore, neither talking or chewing will produce error signals.

Ground electrode 3, which is required for the trouble-free operation of differential amplifier DV, is constituted by at least a part of the helmet cushion, preferably that cushion part in contact with the forehead, and consists of an electrically conductive textile web or fabric.

What is claimed is:

1. A head gear manipulator for invalids, comprising a helmet, an arm carrying gripping means mounted on the helmet, electro-motor drive means operating the gripping means in response to muscle movements of an invalid wearing the helmet, wherein the helmet consists of a blank of thermoplastically deformable sheet material having a center portion and a plurality of arms radiating from the center portion, the arms having free ends, and a longitudinally adjustable circular band mounted over the free arm ends and connecting the same, and a mounting affixed to the center portion for holding the arm carrying the gripping means.

2. The head gear manipulator of claim 1, wherein the circular band is elastic.

3. The head gear manipulator of claim 1 or 2, wherein five of said arms radiate from the center portion, two adjacent ones of the five arms having enlarged free ends for enclosing the condyles of the rear head bone of the invalid.

4. The head gear manipulator of claim 3, wherein two opposing arms have free ends arranged to contact the temples of the invalid, and further comprising an electrode adjustably mounted on the free end of one of the opposing arms and a myoelectric control for the drive means connected to the electrodes.

5. The head gear manipulator of claim 4, wherein the electrode resiliently contacts the temple.

6. The head gear manipulator of claim 4, wherein one of the arms between the opposing arms is arranged to contact the forehead of the invalid, and further comprising a cushioned ground electrode mounted on the free end of the one arm.

7. The head gear manipulator of claim 6, wherein the free end of the one arm is enlarged.

8. The head gear manipulator of claim 1 or 2, wherein the mounting has a spherical socket, and further comprising a holer wherein the arm carrying the gripping means is inserted, the holder having a ball frictionally held in the socket against free movement.

9. The head gear manipulator of claim 8, further comprising a stem connecting the ball to the holder, the spherical socket defining two diametrically opposed slots having a width corresponding to the diameter of the stem.

* * * * *